(12) United States Patent
Jeffrey

(10) Patent No.: US 7,297,135 B2
(45) Date of Patent: Nov. 20, 2007

(54) HOLLOW NEEDLE APPLICATORS

(75) Inventor: Peter Jeffrey, Liverpool (GB)

(73) Assignee: Safe-T Limited, Lonan (GB)

( * ) Notice: Subject to any disclaimer, the term of this patent is extended or adjusted under 35 U.S.C. 154(b) by 111 days.

(21) Appl. No.: 10/536,992

(22) PCT Filed: Dec. 12, 2003

(86) PCT No.: PCT/GB03/05424

§ 371 (c)(1),
(2), (4) Date: Jun. 16, 2005

(87) PCT Pub. No.: WO2004/054644

PCT Pub. Date: Jul. 1, 2004

(65) Prior Publication Data

US 2005/0288633 A1    Dec. 29, 2005

(30) Foreign Application Priority Data

Dec. 17, 2002  (GB)  ................................. 0229345.4

(51) Int. Cl.
*A61M 5/00*   (2006.01)
*A61M 5/20*   (2006.01)
*A61M 5/32*   (2006.01)
(52) U.S. Cl. .................. 604/110; 604/136; 604/198
(58) Field of Classification Search ........... 604/110, 604/130, 131, 133–136, 138, 139, 156, 157, 604/197, 198, 218, 232
See application file for complete search history.

(56) References Cited

U.S. PATENT DOCUMENTS

| | | | |
|---|---|---|---|
| 5,330,430 A | | 7/1994 | Sullivan |
| 5,658,259 A | * | 8/1997 | Pearson et al. ............. 604/232 |
| 5,695,472 A | * | 12/1997 | Wyrick ....................... 604/136 |
| 5,779,677 A | | 7/1998 | Frezza |
| 5,843,036 A | | 12/1998 | Olive et al. |
| 5,957,897 A | * | 9/1999 | Jeffrey ........................ 604/223 |
| 6,015,396 A | * | 1/2000 | Buttgen et al. ............. 604/192 |
| 6,241,709 B1 | | 6/2001 | Bechtold et al. |
| 6,280,421 B1 | * | 8/2001 | Kirchhofer et al. ......... 604/218 |
| 2001/0005781 A1 | | 6/2001 | Bergens et al. |
| 2001/0049496 A1 | | 12/2001 | Kirchhofer et al. |

\* cited by examiner

*Primary Examiner*—Kevin C. Sirmons
(74) *Attorney, Agent, or Firm*—Dennison, Schultz & MacDonald

(57) ABSTRACT

A fluid filled cartridge having a fixed needle and a piston assembly for expression of its contents is mounted inside an applicator. In order to extend the needle from the body prior to cartridge contents expression and without premature leakage of fluid therefrom, an actuator is mounted in the body to drive the cartridge forwards. This is accomplished by co-operating driving and driven parts of the actuator and the cartridge (or any carrier it may have) which are decoupled by release formations in the applicator body after the cartridge has been moved sufficiently to extend the needle. The applicator also includes provision for automatic needle retraction after cartridge contents expression. A separate inventive feature is the deformability of the piston so that force transmission to the trigger means to initiate needle retraction only occurs upon full content expression when the piston has "bottomed out" within the cartridge.

3 Claims, 7 Drawing Sheets

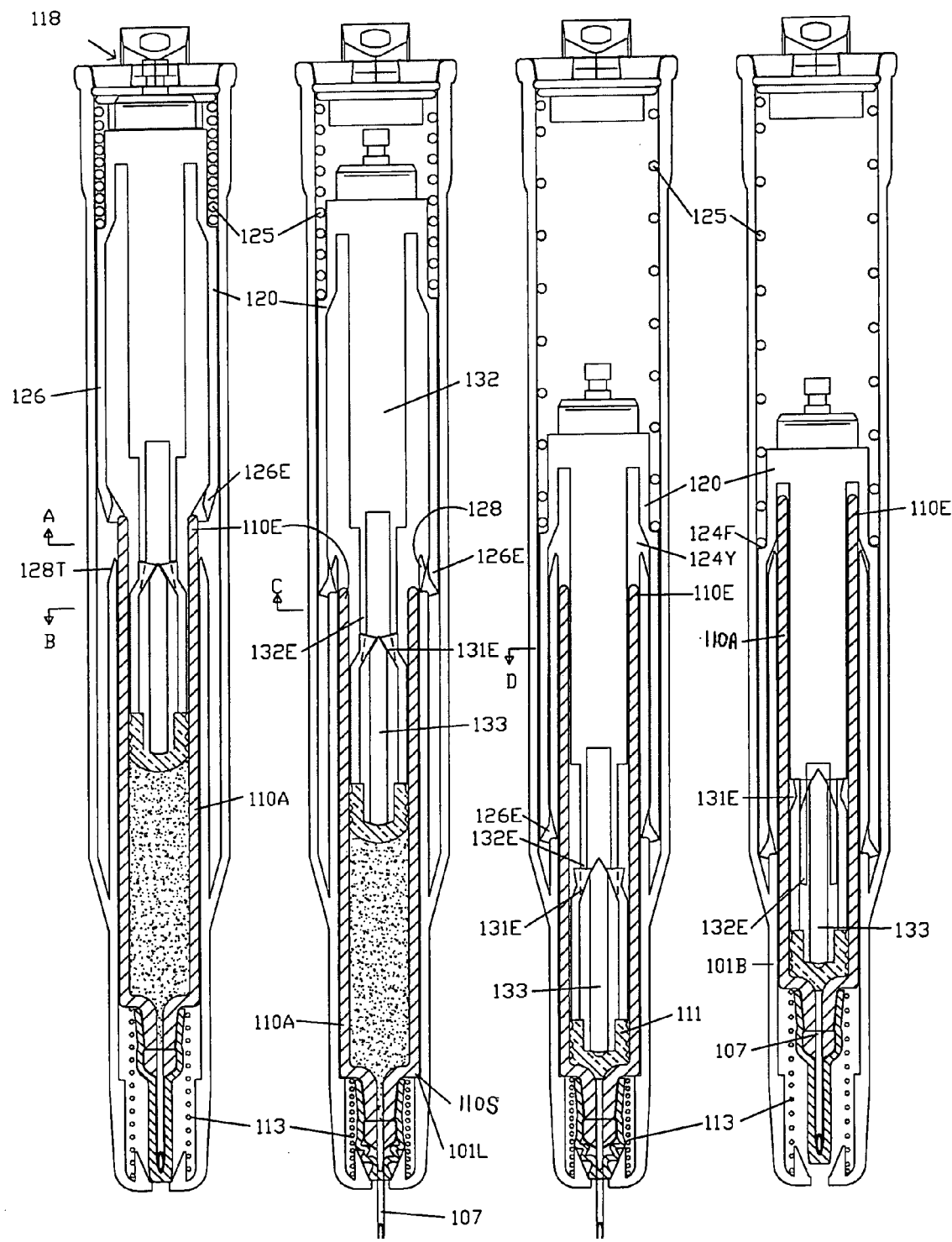

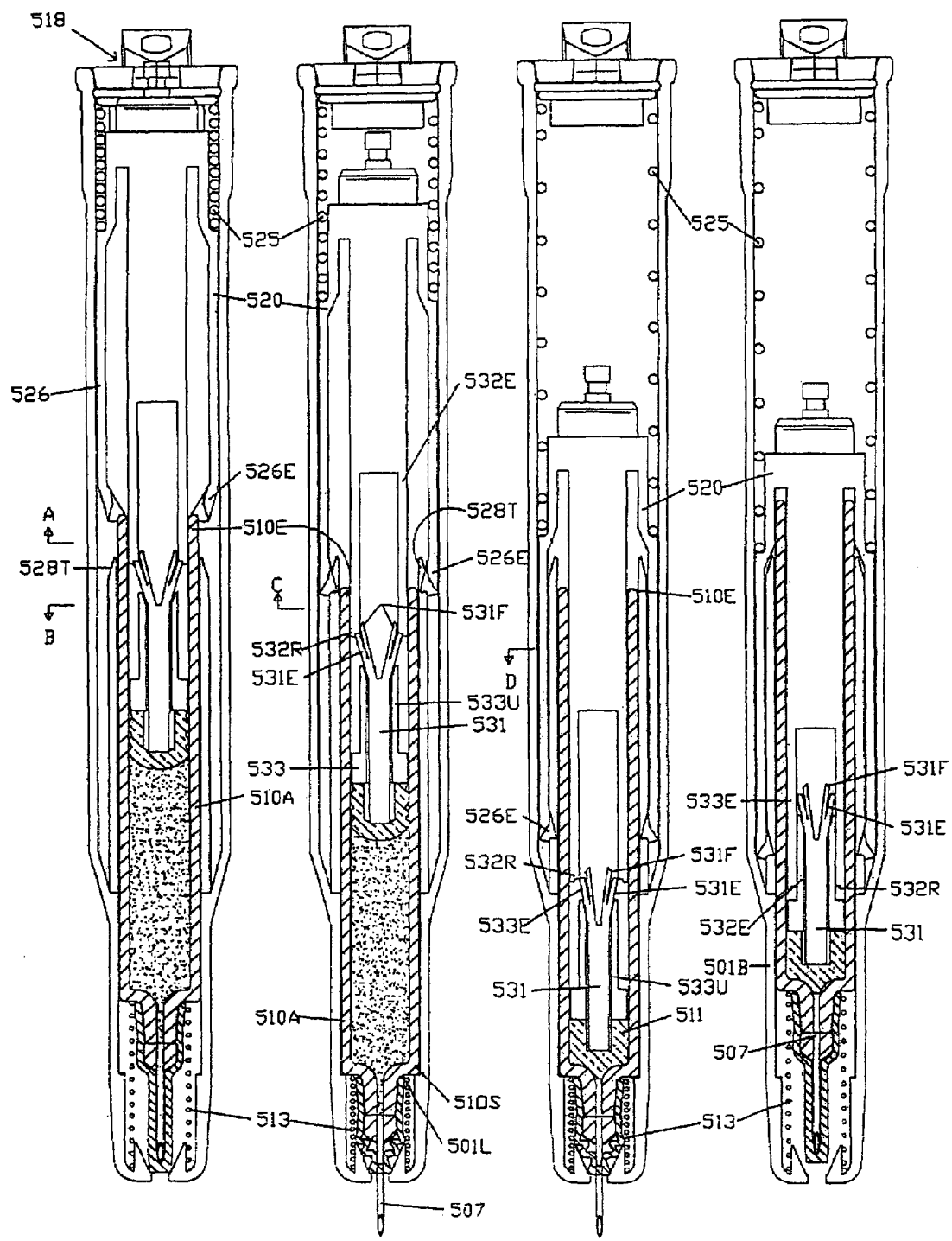

HOLLOW NEEDLE APPLICATORS

This application is a 371 of PCT/GB2003/005424 filed on Dec. 12, 2003.

FIELD OF INVENTION

This invention relates to hollow needle applicators suitable for administering cartridged drugs etc, particularly but not exclusively in a manner assuring retraction of the needle after use.

In using the term "drugs etc" herein, there is no intention to limit application of this invention to drugs or medicaments as such. This invention is generally applicable to any usefully injectable substance and to injecting any appropriate receiver, whether or not that is tissue of a human or animal subject.

Suitability for use in administering drugs does, however, bring in certain constraining desiderata. One is for exceptional reliability as to accuracy of the administered quantity of drug precisely as and where intended. Another is for minimising costs of applicators as essentially one-use throwaway items. Other than springs, component parts need to be individually suited to high-speed plastics injection moulding, and collectively suited to high-speed automated assembly.

BACKGROUND TO INVENTION

Prior proposals for such applicators include providing for needle extension as a first stage in their use, i.e. having an as-supplied state with the needle retracted. Cartridges supplied pre-filled with a measured drug dose typically have fixed needles, in which case such first stage involves movement of the cartridge internally of the applicator. It is known for such movement to be by the same drive force as serves to discharge the cartridge contents through the needle by continuation of such force application through and after cartridge movement for needle extension. It is further known, in relation to typical cartridges having a piston for expression of contents, for drive force application to rely on force transmission through incompressible liquid contents of the cartridge to achieve the first needle extension stage of movement of the cartridge. Examples include EP0516473, which clearly accepts drug weepage through its needle during extension as an inevitability, and also our own earlier WO93/23098 and WO95/35126.

OBJECTS OF INVENTION

An object of this invention is to provide an applicator which does not rely entirely on transmission through cartridge contents for initial needle extending cartridge movement so as to obviate premature contents expression on the way to the needle reaching desired tissue penetration.

Another object of this invention is to minimize, indeed virtually eliminate, ullage requirement. The term ullage is used to refer to the amount by which the cartridge has previously had to be overfilled in order to deliver the predetermined dose because it has not hitherto been possible to deliver the entire contents of a cartridge. There has always been at least a small amount remaining in the cartridge and needle after the piston has been displaced to its full extent, and after the needle has automatically retracted in applicators which have such provision.

SUMMARY OF INVENTION

According to one aspect of this invention there is provided a hollow needle applicator for administering a fluid from a cartridge which has a fixed needle comprising an applicator body in which the cartridge, including its needle, is mounted, a force applying actuator mounted in the body for movement therein to drive the cartridge or a carrier for the cartridge forwards to extend the needle from the applicator body, in which respect the actuator and the cartridge, or its carrier, have co-operating driving and driven parts, and release formation means provided in or on the body to release the said co-operating parts after predetermined movement of the cartridge to extend the needle from the applicator.

In preferred embodiments of the invention the release formation means are arranged to deflect the co-operating driving part of the actuator outwardly of the co-operating driven part of the cartridge or its carrier. This is because preferred practical embodiments of applicator all include means for retraction of the needle after use. This means that an inner region of the applicator body must be kept clear to provide for reception, upon retraction, of piston means and the cartridge body, to which the needle is attached. In embodiments which might be envisaged where some form of needle protection is employed in place of automatic retraction after use, the drive part of the actuator could be deflected inwardly as it is decoupled from the co-operating driven part of the cartridge.

The movement of the cartridge to extend the needle from the applicator may be predetermined, or may be additionally limited, in any one or more of three ways, namely, by full compression of a spring which will act in subsequent needle retraction and is located in a forward end of the applicator body, by abutment of a shoulder on the cartridge with a ledge inside the applicator body, or by abutment of a shoulder on the cartridge, e.g. where a needle holder overlies the main cartridge body, with a needle guide at the forward end of the applicator body.

In preferred embodiments, the same drive force as achieves said predetermined movement can thereafter continue to act in discharging the contents of the cartridge, but does not so act relative to cartridge contents during said predetermined movement. In other words, said drive force advantageously has no action on and applies no force to in-cartridge means (typically of piston type) for discharge pressuring of cartridge contents until positive releasing of the co-operating driving and driven parts of the actuator and cartridge, respectively, takes place.

Suitable driving and driven parts can be provided by extensions from the actuator and from the cartridge beyond its occupation by its contents (or from any carrier for such cartridge), respectively. Typically such extensions will be oppositely directed and will co-operate by direct engagement prior to positive disengagement by the release formation means. However, it would be possible to have indirect engagement between these parts by way of some intermediate part(s), such as a rotatable, apertured drive coupling ring, which is/are movable by the release formation(s).

Suitable release formation means comprises at least one deflector element projecting internally of the applicator body at a position axially along the applicator body that the cartridge or its carrier reaches in said predetermined movement for needle extension.

Disengagement of the driving and driven parts can, in some embodiments, be by movement of an intermediate part, for example by part rotation of an apertured member, such as the aforementioned drive ring or a slotted disc, the slots of which are then brought into registration with the driving and/or driven parts.

Preferred actuators have additional force-transmitting part(s) which are ineffective until the mechanical coupling for needle extension is released, and which become effective to pressurise cartridge contents only after such release. Thus, preferred drive actuators, have two force-applying parts for different purposes, one for needle-extension movement of the cartridge and the other for discharging the contents of the cartridge.

Suitable force-applying parts can be in the form of different extensions of or from the actuator, for example of axial-parallel nature relative to the actuator and the applicator main body part accommodating the actuator, and one being radially inside the other.

Provision for discharging cartridge contents is preferably in conjunction with provision of means for achieving automatic needle retraction after such discharge. This further means advantageously also includes releasable mechanical coupling between the other force-applying part(s) of the actuator and a piston of the cartridge. Moreover, it can be particularly advantageous for the related actuator extension as driving part and the piston rod as driven part to be relatively entrant each other at coupling release.

Positive release of this coupling is advantageously triggered by deformation of the cartridge piston when it reaches the end of the cartridge at the end of intended contents discharge. This necessitates the cartridge piston being formed of suitable deformable material. Also, at the end of contents discharge there must still be substantial force available from the actuator drive spring, for example up to 50% or more compression remaining, preferably about 60%. This can assure that substantially all of the cartridge contents is discharged through the needle, so that virtually no more than needle content is undischarged. This is important for highly expensive drugs as an ullage requirement has hitherto been the norm, i.e. the cartridge having over-fill by as much as 5%-10% compared with actual desired dose as delivered, which may need to be very accurate indeed.

The aforesaid feature, whereby needle retraction is triggered only upon deformation of the piston as it "bottoms out" within the cartridge, thereby assuring virtually entire cartridge contents discharge, is a separate aspect of the invention. It may be employed in other embodiments quite independently of any needle extension provision, whether by drive transmission to the cartridge (or a carrier for same) or via pressure on liquid contents of the cartridge.

Thus, according to a second aspect of this invention there is provided a hollow needle applicator for administering a fluid from a cartridge which has a fixed needle comprising an applicator body in which the cartridge is mounted, a piston assembly located within the cartridge and slidable therein to discharge the fluid contents of the cartridge via the needle, a force applying actuator mounted into the body and having at least one force transmitting part which provides a coupling with the piston assembly effective to displace the piston assembly within the cartridge to discharge contents of the cartridge, provision for automatic needle retraction after cartridge contents discharge comprising spring means arranged within a forward portion of the applicator body to act between the applicator and the cartridge to which the needle is fixed, and means for release of the coupling between the force transmitting part or parts of the actuator and the piston assembly, characterised in that the piston assembly comprises a deformable piston, a piston rod which transmits force to the piston from the actuator and triggering means which is movable by the piston, when deformed into the end of the cartridge, to release the coupling between the force transmitting part of parts of the actuator from the piston assembly and bring about needle retraction.

Release of the aforesaid force-transmitting relation between the second actuator extension and the cartridge piston rod may be by deflection for directly engaging parts or by movement of an intermediate member from drive-transmitting blockage to unblocking of at least some of the driving/driven parts concerned, again as exemplified by use of an apertured drive ring or slotted disc.

One suitable length-shortening provision comprises a piston rod with driven coupling extension parts designed to be deflected away from each other or outwardly for coupling release and a triggering rod slidable in bore through the piston rod to spread those parts when the piston is deformed at reaching the end of the cartridge.

Another suitable length-shortening provision comprises a piston rod with driven coupling extension parts to be deflected towards each other or inwardly for coupling release and a triggering collar slidable about the piston rod to clench those parts when the piston is deformed at reaching the end of the cartridge.

BRIEF DESCRIPTION OF DRAWINGS

Exemplary specific embodiments of this invention are shown in and described relative to the accompanying diagrammatic drawings, in which:

FIGS. 3A to D show stages of operation of the first embodiment;

FIGS. 6A to D show stages of operation of the second embodiment;

DESCRIPTION OF ILLUSTRATED EMBODIMENTS

Figure 1:
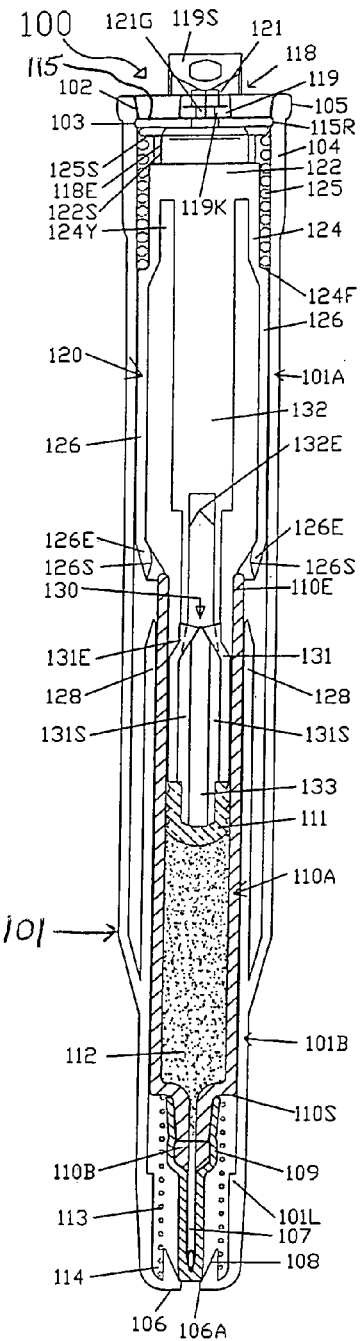
FIG. 1 is an axial sectional view of a first embodiment.

In the drawings, referring first to FIGS. 1 and 2A to D, an applicator 100 is shown as having a hollow generally cylindrical body comprising a main portion 101A and a relatively short forward portion 101B of reduced section, the whole body 101A, B being designed for being moulded in one piece. The applicator body may have a cross-sectional shape other than circular. For example, oval or polygonal or irregular shapes are equally feasible.

The main body portion 101A terminates in an open end 102 which is shown with a slight flare beyond an internal peripheral groove 103 and with an external thickening grip formation 104 below an end bead 105. The reduced section forward portion 101B terminates in a returned end face 106 which is shown centrally apertured at 106A for passage of a hollow needle 107 through an inwardly flared re-entrant portion 108. The latter retains a needle shield 109 that in use is typically made of non-curing elastomeric material and pierced by extension of the needle 107.

The needle 107 and the shield 109 are shown fitted to a reduced end 110B of a hollow generally cylindrical cartridge which has a main portion 110A slidable in the applicator body 101 including its forward portion 101B. The reduced cartridge portion 110B is shown as having a slightly enlarged end to aid retention of the needle shield 109.

The main cartridge portion 110A has pre-loaded contents 112 and a piston 111 therein and it extends (110E) beyond the full contents-accommodating position of the piston 111. An alternative to the cartridge being so extended (110E) would be for such extension to be of a carrier or holder for a standard cartridge. The piston 111 is of deformable material as will be described in relation to maximising expression of cartridge contents 112. An exterior shoulder 110S between the main and reduced portions 110A, B of the cartridge is acted upon by a compression spring 113 which is seated at 114 about the re-entrant portion 108 of the forward body portion 101B. This compression spring 113 can further compress to allow cartridge movement up to abutment of the cartridge shoulder 110S (or part of a cartridge carrier/holder) against an internal ledge 101L of the applicator body portion 101B as will be described for needle extension.

The internal groove 103 around the other end 102 of the main body portion 101A aids secure location by external ribbing 115R of a plug 115 which incorporates a releasable capture provision 118 for an actuator 120. The illustrated capture provision 118 is operative relative to a neck reduction groove 121G in an end extension 121 of the actuator 120, conveniently by way of a slider part 119 with a key-hole aperture 119K that holds or releases the actuator extension 121 according to slider position controlled by a knob or button 119S. However, a slider operating knob or button as illustrated at 119S is neither essential nor particularly preferred for operation of an applicator in accordance with the invention. An arrangement for push-operation from a side of the body part 101A short of its end may well be preferred for at least some practical implementations.

The capture provision 118 shown includes a plug having an inward extension 118E. This provides recessed seating 122S for a head part 122 of the actuator 120 below the neck-grooved part 121 and also outer seating 125S for an actuator drive spring 125 which acts on outward flanging 124F of a main actuator part 124 extending from the head part 122.

It will be appreciated that the drive spring 125 cannot move the actuator 120 until the extension part 121 is released from the capture provision 118.

The objectives of such released movement of the actuator 120 includes first to move the cartridge (110A, B) for needle extension without reliance on application of force to the cartridge piston 111 thus not on force transmission through the cartridge contents 112, i.e. without involving either static friction of the piston or hydraulic lock, and secondly, only after such needle extension, to apply force to the cartridge piston 111 in pressuring the cartridge contents 112 for discharge through the needle 107.

For achieving the first objective, FIG. 1 shows a releasable mechanical coupling between a driving part in the form of extensions 126 from the flanging 124F of the main actuator part 124 and a driven part in the form of the extension 110E of the cartridge (110A, B) beyond the full pre-load position of the cartridge piston 111.

The illustrated releasable coupling mechanism involves the ends 126E of the actuator coupling extensions 126, which are, as shown, inclined radially inwardly for force-transmitting engagement with the registering cartridge extensions 110E, being releasable from such drive force transmitting engagement by radially outward deflection. This releasing deflection involves positive deflecting action by release formations in the form of deflector elements (also termed triggering extensions) 128 which project internally of the main body part (101A, B) of the applicator. Specifically, these triggering extensions 128 are axially parallel projections from the reduced section of the forward body portion 101B into the main body portion 101A immediately around the main cartridge part 110A, thus also having advantageous sliding and locating relation therewith.

Feasible variations on this releasable coupling (126E/110E) include the cartridge (110A, B) being provided in a carrier which has the coupling extensions. Additionally or alternatively the radially relatively inward and outward relationship between the coupling extensions 126E and 110E could be reversed, i.e. the cartridge or carrier coupling extensions 110E could be outward of the actuator coupling extensions 126, 126E and the triggering extensions 128 could be radially located to suit. Additionally or alternatively the release deflection could be of the ends of the cartridge or carrier coupling extensions 110E, either alone or conjointly with some end deflection of the actuator coupling extensions 126.

Figure 2A:
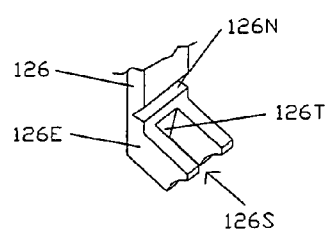
FIGS. 2A to C are related detail scrap views.

FIG. 2A shows the deflectable ends 126E of the actuator coupling extensions 126 as having a hinge notch 126N shown open in FIG. 2A but closed in FIG. 1, and part-bifurcation slotting 126S and tapering 126T to aid co-operation with end tapering 128T of the triggering extension(s) 128. The slotting 126S will accommodate the triggering extensions 128.

As should be apparent from FIG. 1, but see also FIGS. 3A/B, the needle, extending movement of the cartridge 110A, B is accompanied by compression of the retraction spring 113, and is by an amount pre-set to achieve abutment of the cartridge shoulder 110S and the internal ledging 101L of the forward body portion 101B. Strict coincidence between achieving this abutment and completing positive release action of the triggering extensions 128 is desirable but is not essential.

One way to assure mechanical coupling right up to cartridge-arresting abutment is to use a two-stage releasable mechanical coupling, having a first stage along the lines described above but with another drive coupling element that is not so positively disengaged but will disengage automatically when the cartridge is finally arrested by abutment. Such other coupling element will have a load-bearing requirement less than that of the positively disengaged elements as the drive spring will be extended near to its maximum for needle extension.

Figure 2B:
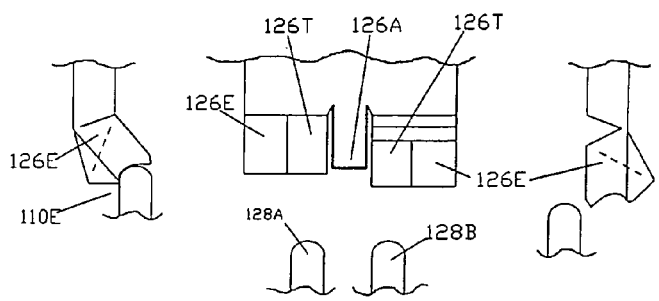
Figure 2C:
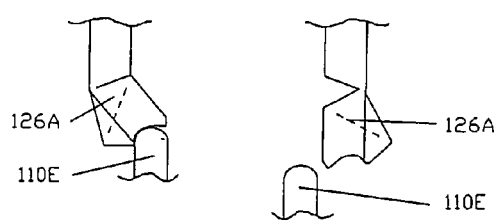

FIG. 2B and 2C in its various components shows a two-stage releasable mechanical coupling with an additional independently deflectable extension leaf 126A between those 126E positively deflected by spaced parallel triggering extensions 128A, B and with its end shaped for less purchase on co-operating coupling extension 110E so as to deflect for decoupling simply by reaction to arrest of the cartridge 110. For illustrative purposes only, FIGS. 2B and C show undeflected coupling engagements to the left and deflected disengagements to the right.

The second actuator objective, namely operation of the cartridge piston 111 to discharge the cartridge contents 112 through the needle 107, also involves a releasable force-transmitting coupling, this time associated with a cartridge piston rod 131. Specifically, the engaged force-transmitting state of this coupling 130 is between deflectable coupling extensions 131E of the cartridge piston rod 131 and coupling extensions 132E of a centrally extending actuator part 132. The piston rod 131 is hollow about a trigger rod 133, which goes to a point at its rear end. This trigger rod 133 can slide axially in the hollow piston rod 131 to deflect the coupling extensions 131E of the piston rod 131 in release of the mechanical coupling 131E/132E. This release action is dependant on the cartridge piston 111 reaching the end of the internal contents-accommodating space of the cartridge (110A, B) and being deformed there to move the trigger rod 133 as well as assure maximal discharge of the contents 112 of the cartridge 110A, B.

The coupling extensions 131E can be inverted forms of what is shown in FIGS. 2A to 2C including bifurcation if the trigger rod 133 is longitudinally ribbed, ridged or splined, i.e. with any such ribbing, ridging or splining accommodated in such bifurcations.

What is shown in FIG. 2A is well suited to embodiments with three or four angularly spaced sets of inter-acting coupling extensions for each releasable mechanical coupling, typically equi-spaced about the applicator axis. However, two each is practical, as in FIGS. 4A to D to be described later.

Sequential operation of the applicator of FIG. 1 is shown in FIGS. 3A to D. In the as supplied state in FIG. 3A the actuator 120 is held by the capture/release provision 118, the actuator drive spring 125 fully compressed, the mechanical coupling 126E/110E engaged and the releasable mechanical coupling 131E/132E also engaged. In the released state shown in FIG. 3B the actuator 120 has been moved by the drive spring 125 to complete needle extending cartridge movement at abutment of the cartridge shoulder 110S with the body ledging 101L, and release of the actuator/cartridge drive coupling 126E/110E by the triggering extensions 128. In FIG. 3C discharge of the cartridge contents 112 has taken place with the mechanical coupling 131E/132E still engaged up to deformation of the piston 111 and release of the coupling 131E/132E by the trigger rod 133 deflecting the piston extensions 131E. Finally in FIG. 3D retraction of the discharged cartridge 110A, B and its needle 107 fully into the body part 101A, B has taken place. The coupling extensions 132E of the actuator 120 have accordingly entered the cartridge piston space 131S about the trigger rod 133, and the cartridge or carrier coupling extensions 110E as well as the trigger extensions 128 have passing through an actuator flange 124F and into an actuator slot 124Y (started at FIG. 3C stage).

Figure 4A:
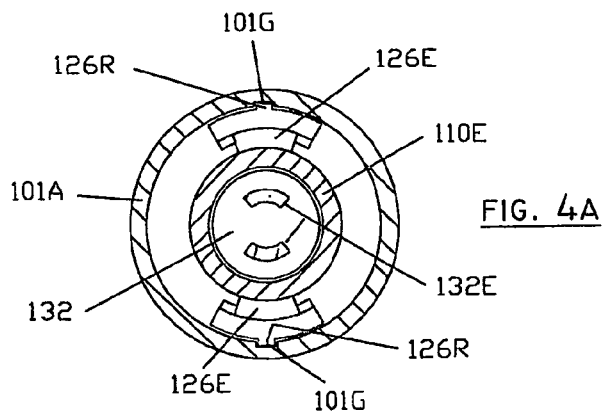
FIGS. 4A to D are cross-sectional views at A to D of FIGS. 3A to D.
Figure 4B:
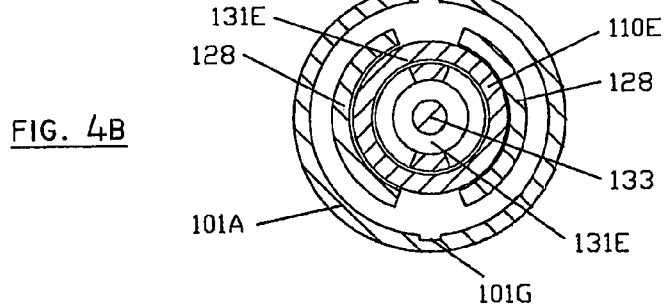
Figure 4C:
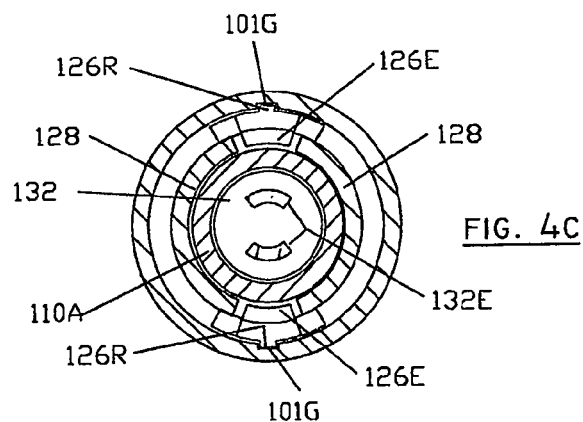
Figure 4D:
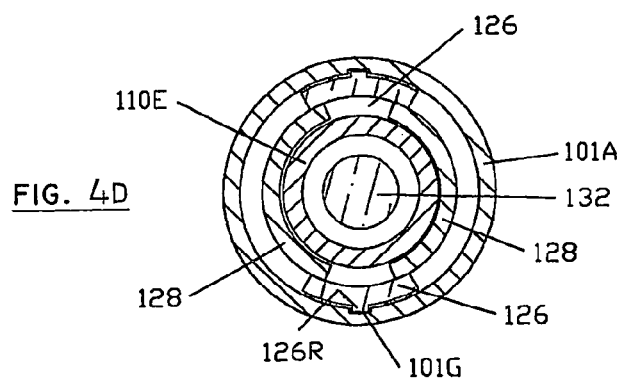

The cross-sections of FIGS. 4A to D show two-element releasable mechanical couplings 126E/110E and 131E/132E, the elements being in diametric relation and with main body guidance by way of ribs and grooves 101G/126R. FIG. 4C shows the coupling extensions 126E deflected into release compared with FIG. 4A, and FIG. 4D shows the actuator part 132 entrant the cartridge or carrier extension 110E compared with FIG. 4B.

Figure 5:
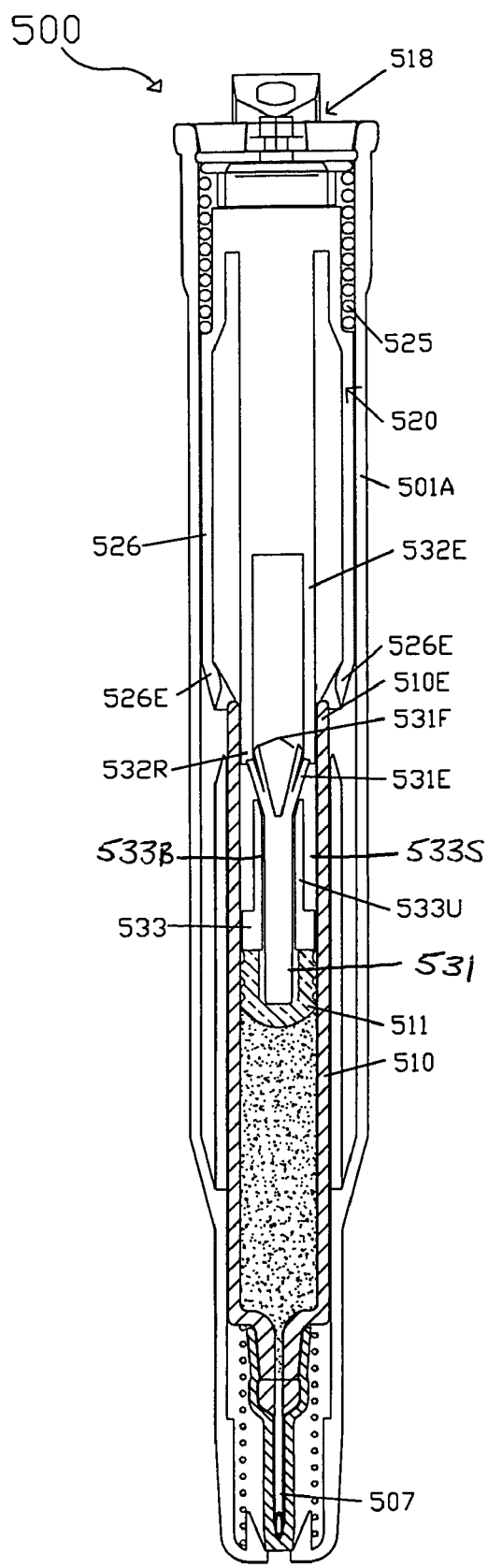
FIG. 5 is an axial sectional view of a second embodiment.
Figure 7A:
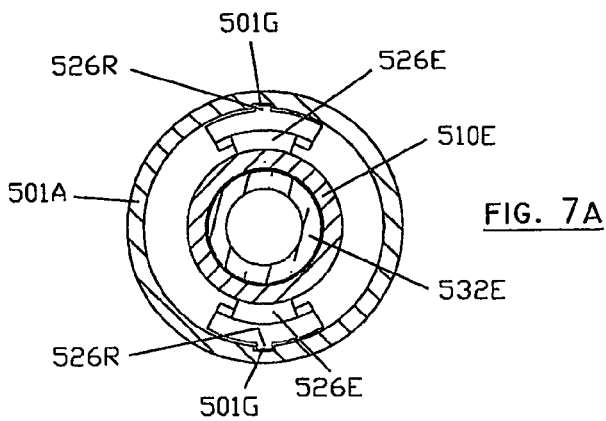
FIGS. 7A to D are cross-sectional views at A to D of FIGS. 6A to D.
Figure 7B:
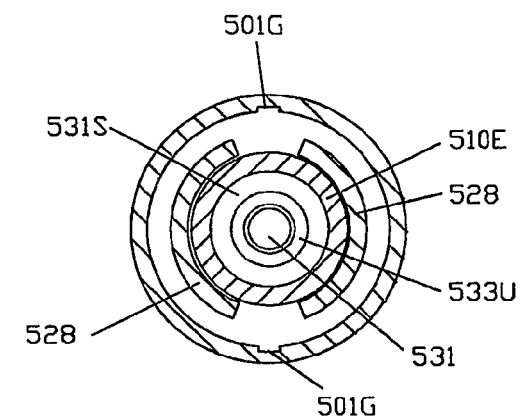
Figure 7C:
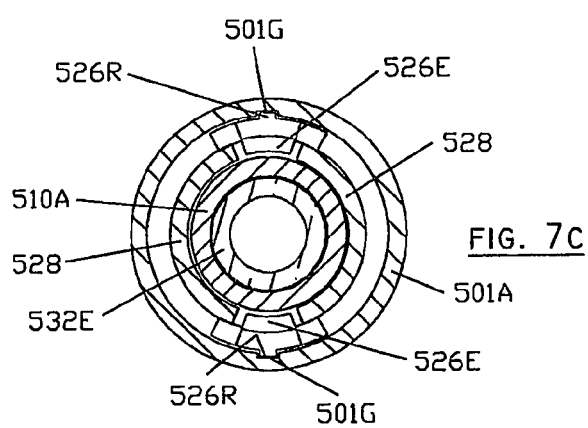
Figure 7D:
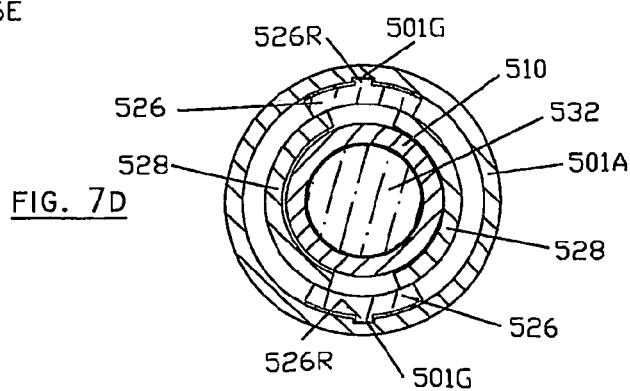

Turning to the second embodiment, as shown in FIG. 5, its differences compared with FIG. 1 lie in the structure for realising the second actuator objective, namely the releasable mechanical coupling involved in cartridge discharge. The actuator 500 is therefore the same as the actuator 100 of FIG. 1 except for its cartridge discharge piston rod 531 being located within a bottom-flanged or inverted top-hat section triggering collar 533. This collar has an axial through-bore 533B and there is a space 533S outside its reduced section upstand 533U for accommodating a tubular extension 532E of the actuator 532 after release of the mechanical coupling which has brought about cartridge contents discharge.

The releasable mechanical coupling shown involves co-operation between a free end rim 532R of the tubular actuator extension 532E and splayed coupling extensions 531E from the inner end of the piston rod 531. The piston rod 531 is able to slide in relation to the collar 533, in its bore 533B, during deformation of the piston 511 when it reaches the end of the cartridge 510. This relative sliding (531/533) results in the collar upstand 533U acting as a trigger ring to bring about release of the coupling 531E/532E, specifically by radially inward deflection of the extensions 531E of the piston rod 531, as is apparent in FIG. 6C.

The coupling extensions 531E of the piston rod 531 are partially split to present longer radially inward extensions 531F for guidance of the end of the actuator tubular extension 532. An alternative would be for the ends of each of the coupling extensions 531E to be stepped.

The releasable coupling 531E/532E is of an essentially similar nature to that already disclosed in our above mentioned PCT applications. Sequential automatic operation of the applicator 500 is believed to be apparent from the stages shown in FIGS. 6A to D, in which reference numerals for corresponding parts have been advanced by 400 compared with FIGS. 1 to 4 other than the specific differences noted above for FIG. 5.

As illustrated for the applicator embodiments of FIGS. 1 to 7, it is feasible and advantageous for the radially offset drive coupling extensions 126, 526 with deflectable ends and their co-operating deflector elements 128 which bring about release after needle extension to be accommodated compactly after such release within consecutive radial spaces inside the coupling extensions 126/526E and the outside triggering extensions 128. Likewise the elements 131/132E (FIGS. 1 to 4) released at cartridge discharge and the elements 532E/533U of FIG. 5 are accommodated in consecutive radial spaces.

Figure 8A:
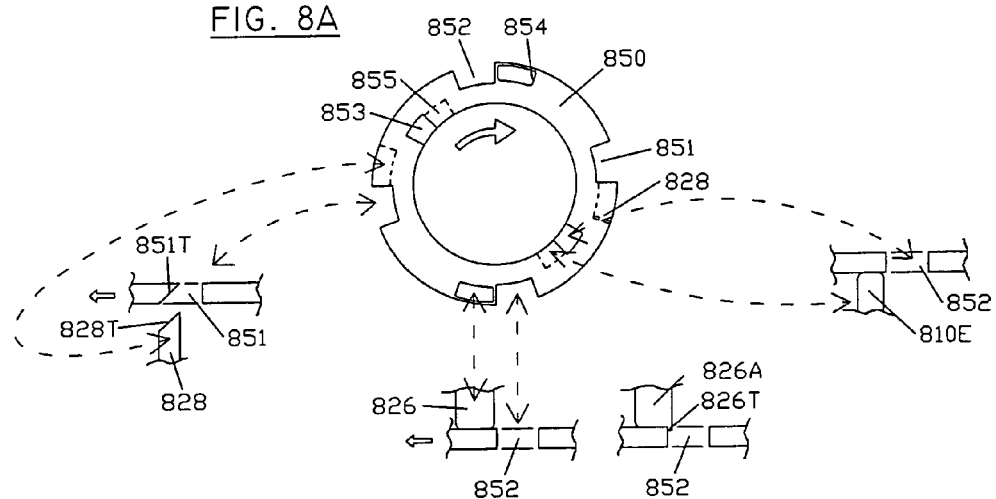
FIGS. 8A to C illustrate details for rotational drive coupling and release, in a third embodiment of the applicator of the invention.

Such radial or transverse compactness can be enhanced to the extent of effectively "losing" one of those thicknesses if the co-operating elements are out of angular registration and their decoupling relies on rotation of an apertured interposed ring, as shown by way of example in FIGS. 8A, B.

Figure 8B:
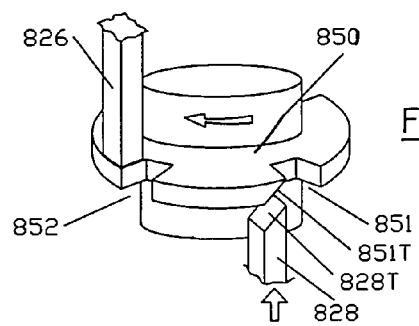

In FIG. 8A, a drive coupling ring 850 has outer angularly spaced apertures 851 and 852 and inner angularly spaced apertures 853. The apertures 851 have side tapers 851T which in use co-operate with side tapering 828T of triggering extensions 828 to rotate the ring 850 to a position where the apertures 851 afford full clearance to the triggering extensions 828. The apertures 852 lie next to drive engagement positions 854 for mechanical coupling extensions 826 from a spring-driven drive actuator (not shown). This drive engagement will prevail until rotation of the ring 850 by the triggering extensions 828 brings the apertures 852 into clearance registration with the drive coupling extensions 826. The inner apertures 853 are next to engagement positions 855 for driven mechanical coupling extensions 810E from a cartridge or carrier therefore (not shown). These apertures will afford full clearance for the driven coupling extensions after rotation of the ring 850 by the triggering extensions 828, to allow a retracted state equivalent to that of FIG. 3D, i.e. overlapping the length of the drive spring engaged part of the actuator 120 without re-compression of the actuator drive spring 125. Although not shown in FIG. 8, the drive spring 125 could engage the ring 850 at the outer apertured part of its width.

Figure 8C:
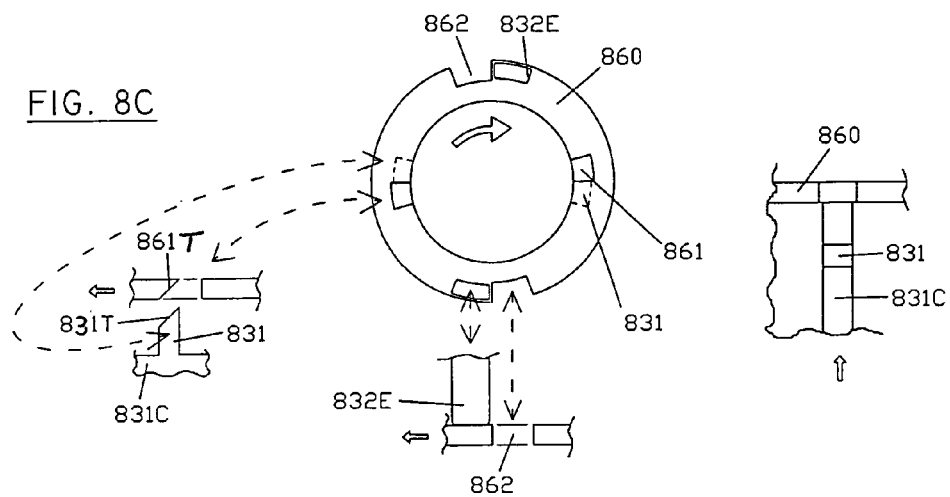

Rotational drive coupling and release is equally feasible for the second mechanical coupling operative for retraction of the discharged cartridge and its needle. Equivalents to outer aperturing 851/852 of FIG. 8A would suffice where the actuator drive coupling extensions and release triggering extensions concerned are angularly spaced at the same radial positions. FIG. 8C shows a drive coupling ring 860 where the triggering extensions 831 are radially inside the actuator drive coupling extension 832E, and outer and inner apertures 862, 861 correspond thereto, respectively. The extensions 831 can be upstands from a collar 831C. As already described for the outer apertures of FIG. 8A, rotation of the ring 860 is by mutual engagement of tapers 831T/861T and results in full clearances 831/861 and 832E/862.

The invention claimed is:

1. A hollow needle applicator for administering a fluid from a cartridge which has a fixed needle, said applicator comprising
   an applicator body in which the cartridge is mounted;
   a piston assembly located within the cartridge and slidable therein to discharge the fluid contents of the cartridge via the needle;
   a force applying actuator mounted into the body and having at least one force transmitting part which provides a coupling with the piston assembly effective to displace the piston assembly within the cartridge to discharge contents of the cartridge; and
   a provision for automatic needle retraction after cartridge contents discharge comprising spring means arranged within a forward portion of the applicator body to act between the applicator and the cartridge to which the needle is fixed;
   wherein the piston assembly comprises a deformable piston, a piston rod which transmits force to the piston from the actuator, and a triggering means which is movable by the piston, when deformed into the end of the cartridge, to release the coupling between the force transmitting part or parts of the actuator and the piston assembly and bring about needle retraction; and wherein
   the piston rod is hollow and has driven extension parts which co-operate with the force transmitting part or parts of the actuator and are deflectable away from each other upon release from said force transmitting part or parts and the triggering means comprises a rod which is slidable within the hollow piston rod to deflect said extension parts.

2. A hollow needle applicator for administering a fluid from a cartridge which has a fixed needle, said applicator comprising
   an applicator body in which the cartridge is mounted;
   a piston assembly located within the cartridge and slidable therein to discharge the fluid contents of the cartridge via the needle;
   a force applying actuator mounted into the body and having at least one force transmitting part which provides a coupling with the piston assembly effective to displace the piston assembly within the cartridge to discharge contents of the cartridge; and
   a provision for automatic needle retraction after cartridge contents discharge comprising spring means arranged within a forward portion of the applicator body to act between the applicator and the cartridge to which the needle is fixed;
   wherein the piston assembly comprises a deformable piston, a piston rod which transmits force to the piston from the actuator, and a triggering means which is movable by the piston, when deformed into the end of the cartridge, to release the coupling between the force transmitting part or parts of the actuator and the piston assembly and bring about needle retraction; and wherein
   the piston rod has driven extension parts which co-operate with the force transmitting part or parts of the actuator and are deflectable towards each other upon release from said force transmitting part or parts and the triggering means comprises a collar slidable about the piston rod to deflect said extension parts.

3. A hollow needle applicator for administering a fluid from a cartridge which has a fixed needle, said applicator comprising
   an applicator body in which the cartridge is mounted;
   a piston assembly located within the cartridge and slidable therein to discharge the fluid contents of the cartridge via the needle;
   a force applying actuator mounted into the body and having at least one force transmitting part which provides a coupling with the piston assembly effective to displace the piston assembly within the cartridge to discharge contents of the cartridge; and
   a provision for automatic needle retraction after cartridge contents discharge comprising spring means arranged within a forward portion of the applicator body to act between the applicator and the cartridge to which the needle is fixed;
   wherein the piston assembly comprises a deformable piston, a piston rod which transmits force to the piston from the actuator, and a triggering means which is movable by the piston, when deformed into the end of the cartridge, to release the coupling between the force transmitting part or parts of the actuator and the piston assembly and bring about needle retraction; and wherein
   the piston rod has driven extension parts which co-operate with the force transmitting part or parts of the actuator and are coupled thereto by way of a drive coupling ring which is provided with spaced apertures and is rotatable by the triggering means to allow passage of the force transmitting and driven extension parts through these apertures.

* * * * *